United States Patent
Ringemann et al.

(10) Patent No.: US 12,042,274 B2
(45) Date of Patent: Jul. 23, 2024

(54) SENSOR DEVICE FOR DETECTING AT LEAST ONE ANALYTE IN A BODY FLUID OF A USER

(71) Applicant: Roche Diabetes Care, Inc., Indianapolis, IN (US)

(72) Inventors: Christian Ringemann, Mannheim (DE); Bernd Steiger, Roemerberg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 896 days.

(21) Appl. No.: 16/175,898

(22) Filed: Oct. 31, 2018

(65) Prior Publication Data
US 2019/0069822 A1 Mar. 7, 2019

Related U.S. Application Data

(63) Continuation of application No. PCT/EP2017/060460, filed on May 3, 2017.

(30) Foreign Application Priority Data

May 3, 2016 (EP) .................................. 16168149

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0004* (2013.01); *A61B 5/746* (2013.01);
(Continued)

(58) Field of Classification Search
CPC ... A61B 5/14532; A61B 5/746; A61B 5/7275; A61B 5/7282
See application file for complete search history.

(56) References Cited

U.S. PATENT DOCUMENTS

| 5,413,690 A | 5/1995 | Kost et al. |
| 5,762,770 A | 6/1998 | Pritchard et al. |

(Continued)

FOREIGN PATENT DOCUMENTS

| CN | 103220966 A | 7/2013 |
| CN | 104755019 A | 7/2015 |

(Continued)

OTHER PUBLICATIONS

International Search Report and Written Opinion, PCT/EP2017/060460, Jul. 20, 2017, 10 pages.

(Continued)

*Primary Examiner* — Christian Jang
(74) *Attorney, Agent, or Firm* — Bose McKinney & Evans LLP

(57) ABSTRACT

A sensor device for detecting at least one analyte in a body fluid of a user. The sensor device includes an evaluation device for evaluating a data stream of time-dependent concentrations c of the analyte. The evaluation device includes a comparator device for comparing a current value c(t) of the concentration c with a first threshold value L and a second threshold value H, wherein H>L. The evaluation device defines a tolerance time interval. Further, the evaluation device, by using the comparator device, is configured to detect if the concentration c rises and exceeds the first threshold value L during the tolerance time interval and to prepare a warning signal W accordingly. The evaluation device is configured to suppress an output of the warning signal W at least until the tolerance time interval expires, under the precondition that c(t)<H during the tolerance time interval.

24 Claims, 3 Drawing Sheets

(51) Int. Cl.
*G08B 21/02* (2006.01)
*G16H 10/40* (2018.01)
*G16H 40/63* (2018.01)
*G16H 50/20* (2018.01)

(52) U.S. Cl.
CPC ............. *G16H 10/40* (2018.01); *G16H 40/63* (2018.01); *G16H 50/20* (2018.01); *A61B 5/14546* (2013.01); *A61B 5/4848* (2013.01); *A61B 5/4866* (2013.01); *A61B 5/7275* (2013.01); *A61B 5/7282* (2013.01); *G08B 21/02* (2013.01)

(56) References Cited

U.S. PATENT DOCUMENTS

| | | |
|---|---|---|
| 5,798,031 A | 8/1998 | Charlton et al. |
| 6,129,823 A | 10/2000 | Hughes et al. |
| 6,360,888 B1 | 3/2002 | McIvor et al. |
| 2003/0125612 A1* | 7/2003 | Fox .................. G16H 15/00 600/347 |
| 2003/0191376 A1 | 10/2003 | Samuels et al. |
| 2005/0013731 A1 | 1/2005 | Burke et al. |
| 2008/0058625 A1* | 3/2008 | McGarraugh .... G01N 33/48792 600/347 |
| 2008/0242962 A1 | 10/2008 | Roesicke et al. |
| 2008/0255438 A1 | 10/2008 | Saidara et al. |
| 2010/0295686 A1* | 11/2010 | Sloan .................. G16H 20/17 703/2 |
| 2010/0317952 A1* | 12/2010 | Budiman ............. A61B 5/4839 600/365 |
| 2014/0121488 A1* | 5/2014 | Budiman ............. A61B 5/7282 600/365 |
| 2014/0350371 A1 | 11/2014 | Blomquist et al. |
| 2015/0065833 A1 | 3/2015 | Bommakanti et al. |
| 2015/0250429 A1 | 9/2015 | Hampapuram et al. |

FOREIGN PATENT DOCUMENTS

| | | |
|---|---|---|
| CN | 105324070 A | 2/2016 |
| CN | 105451639 A | 3/2016 |
| DE | 954712 C | 12/1956 |
| DE | 20020566 U1 | 1/2002 |
| RU | 2552312 C2 | 6/2015 |
| WO | WO 2011/002791 A2 | 1/2011 |
| WO | WO 2011/026053 A1 | 3/2011 |
| WO | WO 2011/041469 A1 | 4/2011 |
| WO | WO 2013/066849 A1 | 5/2013 |
| WO | WO 2014/070456 A1 | 5/2014 |

OTHER PUBLICATIONS

International Preliminary Report on Patentability, PCT/EP2017/060460, Jun. 29, 2018, 11 pages.
Written Opinion of the International Preliminary Examining Authority, PCT/EP2017/060460, Mar. 15, 2018, 10 pages.

* cited by examiner

SENSOR DEVICE FOR DETECTING AT LEAST ONE ANALYTE IN A BODY FLUID OF A USER

RELATED APPLICATIONS

This application is a continuation of PCT/EP2017/060460, filed May 3, 2017, which claims priority to EP 16 168 149.9, filed May 3, 2016, both of which are hereby incorporated herein by reference in their entirety.

BACKGROUND

This disclosure relates to a sensor device for detecting at least one analyte in a body fluid of a user, a sensor assembly for detecting at least one analyte in a body fluid of a user and a method for processing a data stream of a time-dependent concentration of an analyte in a body fluid of a user. The device and methods according to the present disclosure may mainly be used for continuous monitoring of an analyte concentration in a body fluid, such as for long-term monitoring of a blood glucose level or of the concentration of one or more other types of analytes in a body fluid. The disclosure may both be applied in the field of home care as well as in the field of professional care, such as in hospitals. Other applications are feasible.

Monitoring certain body functions, more particularly monitoring one or more concentrations of certain analytes, plays an important role in the prevention and treatment of various diseases. Without restricting further possible applications, the disclosure will be described disclosure in the following text refers to blood-glucose monitoring. However, additionally or alternatively, it can also be applied to other types of analytes.

Blood glucose monitoring, besides by using optical measurements, specifically may be performed by using electrochemical biosensors. Examples of electrochemical biosensors for measuring glucose, specifically in blood or other body fluids, are known from U.S. Pat. Nos. 5,413,690 A, 5,762,770 A, 5,798,031 A, 6,129,823 A or US 2005/0013731 A1.

In addition to so-called spot measurements, in which a sample of a bodily fluid is taken from a user in a targeted fashion and examined with respect to the analyte concentration, continuous measurements are increasingly being used. Thus, in the recent past, continuous measuring of glucose in the interstitial tissue (also referred to as continuous monitoring, CM), for example, has been established as another important method for managing, monitoring and controlling a diabetes state.

In the process, the active sensor region is applied directly to the measurement site, which is generally arranged in the interstitial tissue, and, for example, converts glucose into electrical charge by using an enzyme (e.g., glucose oxidase, GOD), which charge is related to the glucose concentration and can be used as a measurement variable. Examples of such transcutaneous measurement systems are described in U.S. Pat. No. 6,360,888 B1 or in US 2008/0242962 A1.

Hence, besides non-invasive systems, current continuous monitoring systems typically may be transcutaneous systems or subcutaneous systems. Both expressions, in the following text, will be used equivalently. This means that the actual sensor or at least a measuring portion of the sensor is arranged under the skin of the user. However, an evaluation and control part of the system (also referred to as a patch) is generally situated outside of the body of the user, outside of the human or animal body. In the process, the sensor is generally applied using an insertion instrument, which is likewise described in U.S. Pat. No. 6,360,888 B1 in an exemplary fashion. Other types of insertion instruments are also known.

The sensor typically comprises a substrate, such as a flat substrate, onto which an electrically conductive pattern of electrodes, conductive traces and contact pads may be applied. In use, the conductive traces typically are isolated by using one or more electrically insulating materials. The electrically insulating material typically also acts as a protection against humidity and other detrimental substances and, as an example, may comprise one or more cover layers such as resists.

As outlined above, in transcutaneous systems, a control part is typically required, which may be located outside the body tissue and which has to be in communication with the sensor. Typically, this communication is established by providing at least one electrical contact between the sensor and the control part, which may be a permanent electrical contact or a releasable electrical contact. Examples of electrical contacts for contacting a triangular assembly of contact pads are shown, e.g., in DE 954712 B. Other techniques for providing electrical contacts, such as by appropriate spring contacts, are generally known and may be applied.

In order to avoid detrimental effects of the aggressive environment on the conductive properties of the electrical contact, the region of the electrical contact is typically encapsulated and protected against humidity. Generally, encapsulations of electrical locks and contacts by using appropriate seals is known from, e.g., DE 200 20 566 U1. Specifically, in transcutaneous or subcutaneous sensors, in which the region of electrical contact between the sensor and the control part is close to the human skin, an efficient protection against humidity, dirt, sweat and detergents, such as detergents used for body care, is crucial.

Commonly, in order to inform the user about a health status, specifically about a status or a condition wherein the concentration of the analyte in the body fluid is not acceptable, a warning signal has to be provided to the user.

US 2008/0255438 A1 discloses apparatuses and methods for medical monitoring physiological characteristic values such as blood glucose levels for the treatment of diabetes. The apparatuses and methods provide for preventing any negative consequence in the operation of a monitor and/or infusion device as a result of disorientation that may occur from waking from slumber with a low blood glucose level. In addition, a graphical display is disclosed incorporating a variety of enhancements which readily conveys to the user historical as well as real time information regarding the measured characteristic value.

US 2003/0191376 A1 discloses a system and method for extracting a biological fluid from an organism and continuously monitoring its characteristics. The system comprises a tissue interface device suitable for positioning on or about the surface of the biological membrane of the organism and a monitor and control unit coupled to the tissue interface device. The tissue interface device comprises a sensor positioned in a flow path of the fluid for continuously sensing a characteristic of the biological fluid as it flows out from the one or more artificial openings formed in the biological membrane. The sensor generates a sensor signal representative thereof. The monitor and control unit electrically or optically reads the sensor to obtain a measurement of a characteristic, such as concentration of a particular analyte, of the biological fluid on a continuous basis.

US2014/0350371 A1 discloses an apparatus comprising a pump, a user interface, and a controller communicatively coupled to the pump and the user interface. The controller is adapted to receive information relating to a blood glucose level of a user, determine whether the blood glucose level differs from a target blood glucose level by a threshold value, and selectively provide or delay provision of an alert notifying the user to check the user's blood glucose level. Other devices, systems, and methods are disclosed.

WO 2014/070456 A1 discloses systems and methods for providing sensitive and specific alarms indicative of glycemic condition. In an embodiment, a method of processing sensor data by a continuous analyte sensor includes: evaluating sensor data using a first function to determine whether a real time glucose value meets a first threshold; evaluating sensor data using a second function to determine whether a predicted glucose value meets a second threshold; activating a hypoglycemic indicator if either the first threshold is met or if the second threshold is predicted to be met; and providing an output based on the activated hypoglycemic indicator. The system can include a continuous analyte sensor system, sensor electronics, a continuous analyte sensor, and other devices and/or sensors such as medicament delivery pump and meter that can couple with one or more devices.

Despite the advantages and the progress achieved by the above-mentioned developments, specifically in the field of continuous monitoring technology, some significant technical challenges remain. Commonly, the patient or the user may simply suppress or ignore a warning signal when using common sensor devices. This may, for example, happen when the warning signal is output very often and the user does not take the warning signal seriously.

SUMMARY

This disclosure describes sensor device for detecting at least one analyte in a body fluid of a user, a sensor assembly for detecting at least one analyte in a body fluid of a user and a method for processing a data stream of a time-dependent concentration of an analyte in a body fluid of a user. Preferred embodiments, which might be realized in an isolated fashion or in any arbitrary combination, are also described. The disclosed embodiments at least partially address the above-mentioned challenges. Specifically, devices and methods shall be disclosed which allow for a reliable warning signal which indicates for the user that measures have to be taken to decrease the concentration of the analyte to a target range.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, notwithstanding the fact that the respective feature or element may be present once or more than once.

Still further it shall be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "lower threshold limit," "upper threshold limit," "tolerance time value," "offset time interval," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the present disclosure, a sensor device for detecting at least one analyte in a body fluid of a user is disclosed. The sensor device comprises at least one evaluation device configured for evaluating a data stream of time-dependent concentrations of the analyte. The evaluation device comprises at least one comparator device configured for comparing a current value $c(t)$ of the concentration with at least one first threshold value L and with at least one second threshold value H, with H>L. The evaluation device is configured to define a tolerance time interval. Further, the evaluation device, by using the comparator device, is configured to detect if the concentration rises and exceeds the first threshold value L, e.g., at a point in time $t_0$, during the tolerance time interval and to prepare a warning signal W accordingly. Further, the evaluation device is configured to suppress an output of the warning signal W at least until the tolerance time interval expires, under the precondition that $c(t)<H$ during the tolerance time interval.

As generally used within the present disclosure, the terms "patient" and "user" may refer to a human being or an animal, independent from the fact that the human being or animal, respectively, may be in a healthy condition or may suffer from one or more diseases. As an example, the patient or the user may be a human being or an animal suffering from diabetes. However, additionally or alternatively, the teachings of the present disclosure may be applied to other types of users or patients or diseases.

As further used herein, the term "sensor device" generally refers to an arbitrary device configured for conducting at least one analysis, specifically one medical analysis. The sensor device therefore generally may be an arbitrary device configured for performing at least one diagnostic purpose. Specifically, the sensor device may be capable of performing at least one detection of the at least one analyte in the body fluid and/or of contributing to the at least one detection of the at least one analyte in the body fluid. The sensor device, specifically, may be configured for detecting the presence of at least one analyte in a body tissue and/or in a body fluid and/or may be configured for detecting the concentration of at least one analyte in the body tissue and/or in a body fluid.

The term "body tissue" may generally refer to a cellular organizational level intermediate between cells and a complete origin. The body tissue may specifically be an ensemble of similar cells from the same origin that together carry out a specific function. Thereby, organs may then be formed by functional grouping together of multiple tissues. As an example, interstitial tissue, i.e., connective tissue between cellular elements of a structure, may be called a body tissue. As further used herein, the term "body fluid" generally may refer to a fluid which is typically present in a body or the body tissue of the user or the patient and/or which may be produced by the body of the user or the patient. Thus, as an example, the body fluid may be selected from the group consisting of blood and interstitial fluid. However, additionally or alternatively, one or more other types of body fluids may be used, such as saliva, tear fluid, urine or other body fluids.

As further used herein, the term "analyte" may refer to an arbitrary element, component or compound which may be present in the body fluid and the presence and/or the concentration of which may be of interest for the user, the patient or medical staff such as a medical doctor. Particularly, the analyte may be or may comprise an arbitrary chemical substance or chemical compound which may take part in the metabolism of the user or the patient, such as at least one metabolite. As an example, the at least one analyte may be selected from the group consisting of glucose, cholesterol, triglycerides, lactate. Additionally or alternatively, however, other types of analytes may be used and/or any combination of analytes may be determined.

The term "evaluation device" may generally refer to an arbitrary component which is designed to actuate an arbitrary sensor and/or to record signals from the sensor and/or to derive at least one item of information of the analyte from the signals and/or to evaluate these signals in whole or part. The evaluation device may also be referred to as "control part" or as "electronics unit."

Thus, the evaluation device may specifically be or may comprise an electronic component. The electronic component may be configured for one or more of performing a measurement with a sensor, performing a voltage measurement, performing a current measurement, recording sensor signals, storing measurement signals or measurement data, or transmitting sensor signals or measurement data to another device. Thus, the electronic component specifically may comprise at least one of a voltmeter, an amperemeter, a potentiostat, a voltage source, a current source, a signal receiver, a signal transmitter, an analog-digital converter, an electronic filter, an energy storage device, or a data processing device, such as a microcontroller. Other embodiments of the electronic component are feasible. The electronics component may specifically comprise at least one circuit board having disposed thereon elements of the electronics component. Further, the evaluation device may be designed to mechanically hold a sensor and to electrically contact the sensor.

The term "evaluating" may generally refer to an arbitrary process of deriving at least one item of information out of at least one primary item of information such as a signal. Commonly, the term evaluating may comprise analyzing a set of data and/or of least one item of information. Further, optionally, the term evaluating may comprise determining a significance or judging the significance of the set of data and/or of the at least one item of information. Specifically, as further used herein, the term evaluating may comprise deriving at least one item of information of the analyte from at least one signal, specifically from at least one signal provided by the sensor and/or to evaluate these signals in whole or part.

As described above, the evaluation device is configured for evaluating the data stream. The term "data stream" may specifically refer to a sequence or to an assembly of data elements, specifically such as signals, more specifically such as electrical signals, which are available or provided to an arbitrary device over time or in a time-dependent manner. The data stream may be a continuous data stream. However, the data stream may comprise or may have one or more gaps wherein, during the gaps, no data may be transferred to the device. Further, the number of data elements or signals per time unit which are transferred to the device may vary over time.

The term "concentration" may generally refer to an amount of an arbitrary substance in another medium. Specifically, the term "concentration" may refer to an amount of a dissolved or non-dissolved substance in a fluidic medium. The concentration may be described qualitatively, for example, as a mass concentration, as a molar concentration, as a number concentration or as a volume concentration. Thereby, the concentration may be quantified as a mass of the substance divided by the volume of the other medium, as an amount of the substance in moles divided by the volume of the other medium, as a number of the entities of the substance divided by the volume of the other medium and as a volume of the substance divided by the volume of the other medium, respectively. However, other kinds of descriptions may be feasible, such as by using a normality, a molality, a mole fraction, a mole ratio, a mass fraction, or a mass ratio. Thereby, the concentration may be quantified as a molar concentration divided by an equivalence factor, as an amount of the substance divided by a mass of a solvent of the other medium, as an amount of the substance divided by the mass of the other medium, as an amount of the substance divided by a total amount of all components of the other medium, as an amount of the substance divided by a total amount of all other components of the other medium, as a mass of the substance divided by a mass of all components of the other medium and as a mass of the substance divided by a mass of all other components of the other medium, respectively.

Additionally, the concentration of the substance within the other medium may be temperature-dependent, specifically, in case the medium comprises a fluidic medium wherein a volume of the fluidic medium is temperature-dependent.

The term concentration specifically may be a measurement value. The term "measurement value" may generally refer to an arbitrary value which is provided by a measuring device or a sensor device. Specifically, the measurement value may correspond to a value which corresponds to at least one detected signal or which is derived from the detected signal.

As already described above and as further used herein, the term concentration may specifically refer to a concentration of the analyte in the body fluid of the user or the patient. More specifically, the term concentration may refer to a concentration of glucose in the blood of the user or the patient. Typically, the concentration of glucose in the body fluid of a healthy adult person may usually be in the range of 70 mg/dL to 90 mg/dL, which corresponds to 3.9 mmol/l to 5.0 mmol/l. Further, the concentration of glucose in the body fluid of a fasting healthy adult person may usually be in the range of 60 mg/dL to 100 mg/dL, which corresponds to 3.3 mmol/l to 5.6 mmol/l. Commonly, the concentration of glucose in the body fluid may depend on the time of the day.

The concentration of glucose in the blood of the user or the patient may be dependent on events which increase or decrease the concentration of glucose such as an intake of food or physical activity. Thus, the concentration of glucose in the blood may be described as a time-dependent concentration and may be referred to as "c(t)". Generally, the term "time-dependent concentration" may refer to a property of a concentration that varies or changes over time. Thus, when evaluating the concentration at a first point in time, the concentration may have a first value and when evaluating the concentration at a second point in time, the concentration may have a second value which may differ from the first value. The second value may be higher or lower than the first value. However, in certain scenarios, the first value may be equivalent to the second value. The term concentration may also be referred to as "concentration value". Generally, the term "value" may refer to an arbitrary magnitude or to an arbitrary quantity of something.

The term "current value c(t)" may refer to a value of the concentration at a certain point in time or in a particular moment. Specifically, the current value c(t) may refer to a value at a present time, which may be visible or transferred to the evaluation device or optionally also directly to the user or the patient at the present time or only with a small delay. The current value c(t) may represent a single data element of the data stream as described above or may be represent an average value of more data elements of the data stream within a certain, defined time range.

The term "during the time interval" may generally refer to a condition which is fulfilled within an arbitrary time interval, such as the tolerance time interval. Thereby, the condition may be fulfilled during the whole time interval. However, interruptions in satisfying the condition may be feasible in time periods smaller than the time interval; such periods are also referred to as being small. Thus, the time interval may comprise one or more small periods of time wherein the condition is not fulfilled. Specifically, the concentration may exceed the first threshold value L during the time interval but may be below the first threshold value L within small periods of time during the time interval. The concentration may exceed the first threshold value L for the first time at a point in time $t_0$. Thus, as an example, the condition may be fulfilled during more than 90% of the time interval, wherein short interruptions, such as each interruption not exceeding, e.g., 5% of the time interval, may occur and may be ignored. Thus, as will be outlined in further detail below, the time interval may be a relative time interval which is determined by a counter variable. Hence, the time interval is not necessarily an absolute time interval. As long as the condition is fulfilled, the counter variable may be increased, whereas, during times when the condition is not fulfilled, the counter variable may not be increased, may be increased at a lesser rate or even may be decreased. Other options, however, such as options using an absolute time interval, are feasible.

The term "point in time to" may generally refer to a certain moment within a temporal reference system. The point in time $t_0$ may be assignable at an arbitrary time scale. Further, the point in time $t_0$ may have no or only a small temporal expansion.

As described above, the evaluation device comprises the at least one comparator device. As further used herein, the term "comparator device" generally refers to an arbitrary device which is capable of comparing at least two items of information. As used herein, the term "compare" generally refers to the process of deriving at least one secondary item of information out of at least two primary items of information, the secondary item of information indicating a relation between the at least two primary items of information, such as if one of the primary items of information exceeds the other one, which one of the primary items of information exceeds the other one, and the extent by which one of the primary items of information exceeds the other one or the like. As an example, the comparator device may be or may comprise at least one device which is capable of examining or evaluating two or more primary items of an arbitrary set of data or of an arbitrary data stream or of examining or evaluating at least one item of the set of data or of the data stream with at least one other data item or arbitrary information, specifically in order to note similarities and/or differences. The comparator device may be or may comprise at least one software component and/or at least one hardware component. The software component may specifically be capable of performing at least one mathematical operation for conducting examining or evaluating the at least one item of the set of data or of the data stream with the at least one other data item or the arbitrary information. Additionally or alternatively, the comparator system may be or may comprise at least one hardware component.

The term "threshold value" may generally refer to a defined, a predefined or a determinable numeral value which is to be compared with one or more items of information such as with data and/or with measurement values in order to derive at least one secondary item of information. As an example, the threshold value may define a comparison value which is compared with measurement data and/or other items of information, wherein, depending on the comparison, one or more results may be stated. As an example, the threshold value may define a comparison value, wherein, once the at least one item of information reaches the comparison value, exceeds the comparison value or falls below the comparison value, one or more results are stated. The terms "first threshold value" and "second threshold value" may be considered as nomenclature only, without numbering or ranking the named elements, without specifying an order and without excluding a possibility that several kinds of first threshold values and second threshold values may be present. Further, additional threshold values such as one or more third threshold values may be present. As described above, H>L. Therefore, the term "first threshold value L" may also be referred to as lower threshold value, whereas the term "second threshold value H" may also be referred to as higher threshold value. The terms "lower threshold value" and "higher threshold value" may describe a relationship between the two mentioned threshold values relative to each other without defining absolute values for describing a difference between the two mentioned threshold values and without defining a difference to one, or more other values.

Generally, the concentration of the analyte in the body fluid may optimally be within a so-called target range. The term "target range" may refer to a range which is defined by a lower target range threshold value and a higher target range threshold value, wherein the lower target range threshold value is smaller than the higher target range threshold value. The target range may define a desired range for the concentration of the analyte in the body fluid where the user or the patient may be in optimal healthy condition with regard to the desired concentration of the analyte in the body fluid. For example, the target range of glucose within the blood of the user may be in the range of 70 mg/dL to 160 mg/dL, preferably in the range of 80 mg/dL to 140 mg/dL, more preferably in the range of 90 mg/dL to 120 mg/dL. The target range may depend on the time of day. Thus, the target range during the night may differ from the target range during the day. The target range may be defined by default values. Further, the target range may be adjusted by the user. Further, the target range may be selected personally for the user. The first threshold value may specifically correspond to the lower target range threshold value or may be larger than the lower target range threshold value.

The first threshold value may also be referred to as "warning threshold" or as "high warning threshold". Thereby, a concentration of the analyte in the body fluid that exceeds the first threshold value may correspond to a health status of the user which is acceptable at least over a certain time interval but not optimal. Further, the second threshold value may also be referred to as "alert threshold" or as "high alert threshold". Thereby, a concentration of the analyte in the body fluid which exceeds the second threshold value may correspond to a health status of the user which is not acceptable and during which the user or the patient may be in danger with regard to the user's health status. Therefore, the warning signal may be configured to indicate to the user that measures have to be taken in order to decrease the concentration of the analyte in the body fluid, such that the concentration falls at least below the second threshold value and optimally reaches the target range. Alternatively, the first threshold value may be referred to as "notification threshold" and the second threshold may be referred to as "warning threshold."

The first threshold value L and/or the second threshold value H may specifically be chosen by one of the following actions. A default value may be used for the first threshold value L and/or the second threshold value H. Further, the first threshold value L and/or the second threshold value H may be adjusted by the user. Still further, the first threshold value L and/or the second threshold value H may be selected personally for the user. For example, a physician or legal guardian or a supervisor may have an authorization for choosing the first threshold value L and/or the second threshold value H while the user or the patient may not have an authorization for choosing first threshold value L and/or the second threshold value H. For example, the first threshold value L and the second threshold value H may be defined as a default offset value respectively, wherein the default offset values are added to the target range. Thus, in case the target range differs or varies over time, specifically over a day, the first threshold value L and the second threshold value H may vary over time accordingly. Thus, the effort for adjusting the first threshold value L and the second threshold value H may be advantageously reduced for the user or the patient. Moreover, the sensor device itself may be configured to adjust the first threshold value L and the second threshold value on basis of former values in the past successively such that the patient or the user may receive an improved adjustment of these parameters.

The term "rising" may refer to an arbitrary process, wherein an arbitrary value of an item of interest increases when comparing a first value of the item of interest to a second value of the item of interest. Thereby, the first item of interest and the second item of interest may differ from each other by at least one parameter. For example, the first item of interest and the second item of interest may refer to different points in time. Thus, the item of interest may rise in a time-dependent manner. As further used herein, the term rising may be used to describe a possible development of the current value c(t) of the concentration of the analyte over time. However, the current value c(t) may not only rise but may alternatively also decrease or stay at least almost constant, e.g., retain a certain value, at least during a certain period of time, wherein the current value c(t) may only show slight deviations from an averaged value. Further, the term "exceeding" may refer to an arbitrary process, wherein an arbitrary value of an item of interest not only increases but also goes beyond a certain, predefined or predetermined limit value or threshold value.

As further used herein, the term "signal" may refer to an arbitrary indication which is transferable from one element to another element, specifically in order to indicate, warn, direct or to command. Thus, the indication may comprise at least one item of information. Specifically, the signal may be or may comprise at least one of an electronic signal, a visual signal, an acoustic signal or a vibrational signal. Thereby, the electronic signal may be or may comprise an electrical quantity of effect such as a current, a voltage or an electromagnetic wave. The electrical quantity may be variable in such a way in order to convey information.

The term "warning signal W" may refer to an arbitrary signal which is configured to express or to give notice that an arbitrary undesired event has occurred, is occurring or may occur in near future. Specifically, the warning signal W may be configured such that the device or the person to which the warning signal W is transferred may have the ability to react to the warning signal W. Thereby, the term "preparing a signal" may specifically refer to a process of one or more of generating, transferring or internally marking the necessity for generating and/or transferring the signal. As an example, the process of preparing the signal may also contain storing at least one item of information on the necessity for generating and/or transferring the signal in a data storage device, wherein the output of the signal, which will be explained in further detail below, may be a separate process, the performing of which may depend on one or more additional factors and/or conditions.

Consequently, in the context of the present disclosure, the preparation of the warning signal is separated from the output of the warning signal. Thus, in case a warning signal is prepared and, thus, is marked for being generated and/or transferred, the output of the warning signal may depend on one or more additional conditions to be fulfilled, as will be explained in further detail below. Thus, specifically, the evaluation device may be configured for separating the processes of preparing the warning signal and outputting the warning signal.

The process of preparing the warning signal specifically may imply one or more of generating and/or transferring the warning signal, specifically an electronic signal, to another component of a device or to another, further device, wherein the other component of the device or the further device are configured to output the warning signal W.

Further, the term "output of a signal" generally refers to the process of providing and/or transferring the signal to one or more other devices and/or to a user. Thus, the output of a warning signal generally implies providing and/or transferring the warning signal to one or more other devices and/or to a user, such as by one or more of electronic transfer of the warning signal, acoustically providing the warning signal, vibrationally providing the warning signal or visually providing the warning signal. The output of the warning signal specifically may imply giving the user or the patient at least one item of information that an undesired event has occurred, is occurring or may occur in near future. The output of the warning signal may therefore specifically be or may comprise at least one acoustic signal and/or at least one visual signal. Still, other kinds of signals are feasible.

The term "suppressing an output of the warning signal W" may refer to a process of postponing the output of the warning signal W to a later point in time. Thus, as discussed above, the method described herein may imply separating the generation of the warning signal and the output of the warning signal, and the evaluation device according to the disclosure may imply separating the generation of the warning signal and the output of the warning signal, wherein, between these two events or actions, a time interval may occur. Thus, generally, the later point in time may differ from an original point in time, wherein the output of the warning signal W is suppressed during a time interval. Therein, the term "suppressing" generally may imply both the option that the output of the warning signal simply is delayed at least until the later point in time, e.g., until expiry of the time interval, and/or the option that the output of the warning signal is prevented completely. Thus, after expiry of the time interval and/or at the later point in time, the output of the warning signal may depend on one or more conditions to be fulfilled, as will be outlined in further detail below. Thereby, before the warning signal is output, the conditions to be fulfilled may be reviewed and only in case the conditions to be fulfilled are complied with the warning signal is output. Thus, the output of the warning signal is suppressed at least until the tolerance time interval expires. After expiry of the tolerance time interval, the warning signal may simply be output, the output of the warning signal may be delayed further, or the output of the warning signal may be made dependent on one or more conditions being fulfilled. As an example for the latter option, in case the concentration is below the first threshold value L after expiry of the tolerance time interval, the output of the warning signal may be prevented completely.

The term "time interval" may generally refer to an arbitrary period of time, which may be an absolute period in time, such as a period in between a first point in time and a second point in time, or a relative period in time, such as indicated by a time counter variable which increases steadily or unsteadily. Specifically, the term time interval may refer to a space between a first point in time and a second point in time, wherein the second point in time differs from the first point in time. Additionally or alternatively, starting with the first point in time, a time counter variable may be increased, until a predetermined or determinable stop value for the time counter variable is reached, which indicates the expiry of the relative time interval. The time counter variable, as an example, may be increased constantly at a predetermined or determinable rate, or by increasing the time counter variable in regular or non-regular time intervals. The increasing of the time counter variable may also be made dependent on one or more conditions to be fulfilled, such as by increasing the time counter variable only in case the condition $c(t)>L$ is fulfilled, as will be outlined in further detail below.

The above described time interval may also be denoted as "tolerance time interval", wherein within the tolerance time interval a certain event is endured or accepted. Specifically, the tolerance time interval may refer to a time interval during which the concentration is larger than the first threshold value L but smaller than the second threshold value H. In other words, the tolerance time interval describes or denotes how long it is acceptable that the concentration is larger than the first threshold value L. Therefore, the tolerance time interval may also be referred to as "length of stay time" or as a "tolerated time above elevated glucose level or elevated glucose limit."

Further, the term "expiring of the tolerance time interval" may refer to a scenario, wherein at least one third point in time is reached which is outside the time interval which is defined as the space between the first point in time and the second point in time. The term "precondition" generally refers to one or more items which have to be fulfilled or which are necessary before a subsequent result and/or event may occur.

The evaluation device further may comprise at least one data storage device configured for storing a tolerance time value $\Delta t$. As further used herein, the term "data storage device" refers to an arbitrary device which is configured to record and/or to retrieve at least one item of information from an arbitrary medium. Thus, the term data storage device may also be referred to as data processing device. Specifically, the data storage device may be or may comprise an electronic data storage device which commonly requires electrical power to store and to retrieve data. Specifically, electromagnetic data may be stored in either an analog data or digital data format. The type of data may therefore be considered to be electronically encoded data. The data storage device may be configured to permanently store data. Thus, the data may remain stored even in case power is removed from the device. However, other embodiments are feasible. For example, the data storage device may comprise at least one semiconductor device. Further, the data storage device may be or may comprise at least one software component. The software may specifically be capable of performing at least one mathematical operation for recording and/or retrieving the at least one item of information.

The term "tolerance time value $\Delta t$" refers to a length of the tolerance time interval as described above. Specifically, the tolerance time value $\Delta t$ may refer to a difference between the second point in time and the first point in time which were described above. For example, the first point in time may be denoted as $t_0$ and the second point in time may be denoted as $t_{10}$ and the difference between $t_{10}$ and $t_0$ may be $\Delta t$. Therefore, the evaluation device may be configured to preliminarily define the tolerance time interval as $[t_0; t_0+\Delta t]$. Specifically, the evaluation device may be configured to define the tolerance time value $\Delta t$ according to one of the following options:
  a default value is used and stored in the data storage device;
  the tolerance time value $\Delta t$ is personally adjusted for the user and is stored in the data storage device; OR
  the tolerance time value $\Delta t$ is manually adjusted by the user.

The term "default value" may refer to an arbitrary value which may be defined in advance, before the sensor device is applied by the user or the patient for the first time. For example, the default value may be determined by a manufacturer. Thus, a usage of the sensor device by the user or the patient may be facilitated as the number steps which need to be conducted before the sensor device is first applied is reduced. The term default value may thus also be referred to as "standard value."

The term "personally adjusted" may generally refer to an arbitrary process, wherein an arbitrary value is defined or intended for a use of one single person only and may be adapted for the person's needs. The personally adjusted value may take into account special, individual characteristics, circumstances and/or properties of the person. Thus, the personally adjusted value of a first person may be different from the personally adjusted value of a second person. As described above, the tolerance time value Δt may be personally adjusted for the user. Thus, the user or the patient may not necessarily adjust the tolerance time value Δt by himself. Instead, another person such as a physician may adjust the tolerance time value Δt for the user or the patient.

Additionally or alternatively, the sensor device itself may be configured to adjust the tolerance time value Δt for the user or the patient. Thereby, the sensor device may be configured to learn from the past, i.e., from previous data. Thus, the sensor device may be configured to further adjust the tolerance time value Δt and/or other parameters such as the first threshold value L or the second threshold value H successively, such that the patient or the user may receive an improved adjustment of these parameters.

Further, the term "manually adjusted" may generally refer to an arbitrary process, wherein an arbitrary value is defined not automatically but rather by actively conducting a process or a procedure. As described above, the tolerance time value Δt may be manually adjusted by the user. Thus, the user or the patient may specifically adjust the tolerance time value Δt by himself.

The evaluation device may further be configured to recognize at least one point of time $t_1$ at which an event known to have an effect lowering the concentration of the analyte occurs. The term "event" may generally something that happens or is regarded as happening. Thus, the term event may also be referred to as "occurrence." The event may occur in a certain volume or in a certain element such as in a certain medium. Further, the event may take place during a particular interval of time. The term "effect" may generally refer to something which leads to a certain result or consequence. Thus, the effect has an influence on a certain event, process or occurrence. Thereby, the effect may be desired or undesired. The term "lowering" may refer to procedure wherein something is reduced or decreased from an arbitrary volume or medium. Thereby, the term lowering may comprise an active or a passive reduction. Specifically, the event known to have an effect lowering the concentration of the analyte may be selected from the group consisting of: an intake of a medication, specifically an insulin medication; a physical activity of the user, specifically sports. The term "intake of a medication" may specifically refer to an intake via infusion, e.g., via an introduction of the medication through a skin site of the patient or the user via an infusion cannula. The term "physical activity" may refer to an arbitrary activity, wherein a human or animal may move muscles of his or her body. Thereby, the term "sports" may relate to an athletic activity requiring skill or physical prowess which aims to use, maintain or improve physical ability and skills.

Specifically, the evaluation device may be configured to define an offset time interval starting at $t_1$. The term "offset" may generally refer to something that counterbalances, counteracts or compensates something else. The offset time interval may be or may represent a further time interval which is different from the tolerance time interval. The "offset time interval" or simply "offset time" may also be referred to as a lockout time or acting time and may denote an additional time interval during which the output of the warning signal is suppressed. As an example, this additional time interval may be a time interval during which a medication and/or a drug is known to interact with the body of the user and/or a time interval which typically is needed for the medication and/or drug to show an effect on the user and/or on the concentration of the analyte. The evaluation device may be configured to suppress the output of the warning signal W at least until, additionally, the offset time interval is expired, under the precondition that c(t) is below or falls below the second threshold value H but exceeds the first threshold L during the offset time interval. The evaluation device may further be configured to output the warning signal W, if the concentration c exceeds H at any time.

Specifically, the evaluation device may be configured to perform one of the following operations during the offset time interval:
 (a) the warning signal W is always provided when c(t) exceeds the second threshold value H; or
 (b) the warning signal W is never provided when c(t) exceeds the second threshold value H.

In case of option (a), the term offset time interval may therefore also be referred to as "acting time."

Further, the evaluation device may be configured to perform one of the following operations:
 (a) the tolerance time interval is unaffected by the offset time interval, and the output of the warning signal W is suppressed at least until both of the tolerance time interval and the offset time interval have expired;
 (b) the tolerance time interval is suspended until expiry of the offset time interval and restarted for a remaining time after the offset time has expired; or
 (c) the tolerance time interval is reinitialized at $t_1$, preferably by defining an updated tolerance time interval as $[t_1; t_1-\Delta t]$ with Δt being the tolerance time value.

Thereby, the term "unaffected" may refer to a property of something of being free from influences. Thus, the offset time interval may specifically be a time interval which may be configured to start at a point in time while the tolerance time interval may continue independently from the scenario that the offset time interval starts.

The term "remaining time" may refer to an amount of time which differs from an original amount of time and may be smaller than the original amount of time. The remaining time may be a difference between the original amount of time and an already passed time. Specifically, the remaining time may refer to a difference between the rime interval Δt and the already passed time. Thereby, the term "suspended" may refer to a process of stopping or breaking an arbitrary process. Further, the term "restarted" may refer to a process of continuing with a certain action.

The term "updated" may generally refer to a property of an element or of a process of being adapted to a current need or to current circumstances. Thus, the term updated may also refer to a corrected property of the element or of the process. The updated property of the element or of the process may differ from an original property of the element or of the process. Thus, the term "updated tolerance time interval" may refer to a corrected tolerance time interval which may differ from the tolerance time interval. Specifically, as described above, the updated tolerance time interval may be defined as $[t_1; t_1+\Delta t]$. Thus, the updated tolerance time interval may differ from the tolerance time interval by the point in time at which updated tolerance time interval starts. However, an updated tolerance time interval value $\Delta t_2$ may be equivalent to Δt. Thereby, the term "reinitialized" may refer to a property of a process of being set to a starting value or of being set to the beginning of a program or a subprogram of the process that has already been started.

The evaluation device may be configured to choose a length of the offset time interval. The term "choose" may refer to a property of an element or of a value of being selectable and/or changeable or adaptable to special needs. The term "length of the offset time interval" may also be referred to as a value of the offset time interval or as duration of the offset time interval. Specifically, the evaluation device may be configured to choose the length of the offset time interval according to one of the following options:

a default value is used for the length of the offset time interval;

a length of the offset time interval adjusted by the user is chosen;

a length of the offset time interval is selected personally for the user;

a length of the offset time interval is calculated automatically by taking into account a nature of the event known to have an effect lowering the concentration of the analyte, specifically by taking into account a bolus of a medication, more specifically by taking into account an insulin bolus.

For example, the user and/or the other person may determine the length of the offset time interval on basis of a bolus calculator, i.e., on the basis of at least one result calculated by a device configured for determining the required bolus of a medication and/or a drug such as insulin. Specifically, the length of the offset time may be dependent on an amount of the bolus in relation to a difference to the target range. Thus, generally, as used herein, the term "bolus" generally refers to the administration of a specified amount of medication and/or drug in order to adjust the concentration of the medication and/or drug and/or at least one compound influenced by the medication and/or drug to a predetermined or desired effective level. However, other calculation bases for the individual adjustment are feasible.

Further, the evaluation device may be configured to output the warning signal W if the concentration c exceeds the first threshold value L after the tolerance time interval expires and if the current value c(t) of the concentration c is below the second threshold value H during the tolerance time interval. The evaluation device may further be configured to output the warning signal W, if the concentration c exceeds H at any time.

Further, the evaluation device, by using the comparator device, may be configured for detecting if the concentration falls below the first threshold value L during the tolerance time interval. The term "during the tolerance time interval" may refer to one or more points in time t within the tolerance time interval, e.g., $t_0 < t \leq t_0 + \Delta t$.

Specifically, the evaluation device may be configured to perform one of the following operations:

the expiry of the tolerance time interval is aborted when the concentration falls below the first threshold value L and the output of the warning signal W is prevented;

the expiry of the tolerance time interval is suspended as long as the concentration is below the first threshold value L;

the expiry of the tolerance time is slowed down during times in which the concentration is below the first threshold value L; or the expiry of the tolerance time is reset after the time in which the concentration is below the first threshold value L reaches a predetermined threshold.

The above-mentioned operations may refer to a hysteresis of the sensor device. The term "hysteresis" may refer to a phenomenon in which a reaction of an arbitrary system to changes is dependent on past reactions to change. Thus, the sensor device may be configured not only for comparing the current value c(t) of the concentration c with the first threshold value L and the second threshold value H during an absolute time interval with a fixed time range, but, instead, the tolerance time interval may also be regarded as a relative time interval. Thereby, the sensor device may be configured to adapt or to alter the expiry of the tolerance time interval in dependence on a behavior of the current value c(t) during the tolerance time interval.

The term "aborted" may refer to a property of a process of being stopped. Thus, the process may not continue, at least within a certain time interval. The term "prevented" may refer to a property of a process of being hindered or kept from occurring, specifically, before the process has started to occur. The term "reset" may refer to a property of a process of being set to a starting value or of being set to a beginning of a program or a subprogram of the process that has already been started. Thus, the term reset may also be referred to as reinitialized. The term "predetermined" may generally refer to a property of being determined, stated or fixed before a certain event occurs or is introduced.

Further, the evaluation device, by using the comparator device, may be configured to detect if the concentration exceeds the second threshold value H during the tolerance time interval and to prepare a high level warning signal WH accordingly. Specifically, the evaluation device may further be configured to recognize at least one point of time $t_1$ at which an event known to have an effect lowering the concentration of the analyte occurs. More specifically, the event may be selected from the group consisting of: an intake of a medication, specifically an insulin medication or a physical activity of the user, specifically sports, wherein the evaluation device is configured to define a high level offset time interval starting at $t_1$, wherein the evaluation device is configured to suppress an output of the high level warning signal WH at least until the high level offset time interval is expired. The term "high level offset time interval" may refer to a further or to an additional offset time which differs from the offset time as described above. The high level offset time interval may refer to a time interval, where within the time interval the warning signal W is suppressed even if the concentration exceeds the second threshold value. Specifically, the high level offset time interval may be smaller than the tolerance time interval, e.g., a value of the high level offset time interval may be smaller than the tolerance time interval value. Further, the high level offset time interval may be within the tolerance time interval, e.g., the high level offset time interval may start at a point in time prior to a starting time of the tolerance time interval and may end at a point in time subsequent to an end time of the tolerance time interval. However, other embodiments may be feasible.

The sensor device may be configured for receiving a data stream of time-dependent measurement signals from at least one sensor configured for monitoring the time-dependent concentration of the analyte in a body fluid. The term "measurement signal" may generally refer to an arbitrary signal which characterizes an outcome of the detection. The measurement signal may be or may comprise at least one electronic signal such as at least one voltage and/or at least one current. Specifically, the measurement signal may be or may comprise at least one analog signal and/or may be or may comprise at least one digital signal. Further, the measurement signal may correspond to a current value at a certain point in lime to. Specifically, the evaluation device may be configured to transform the data stream of the time-dependent measurement signals into the data stream of time-dependent concentrations of the analyte.

The sensor device may further comprise at least one database, wherein data stream of time-dependent concentrations of the analyte are stored in the database. The term "database" may generally refer to an organized collection of data. Specifically, the database may further comprise additional information on events having an influence on the concentration of the analyte. For example, the additional information on the events having an influence on the concentration of the analyte may comprise at least one item of information selected from the group consisting of: a bolus of insulin; a physical activity of the user, specifically sports; an intake of nutrition.

Further, the sensor device may comprise at least one suppress function. The term "suppress function" may refer to a function of an arbitrary device which may be configured to perform a suppressing according to the above-mentioned definition, specifically a suppressing of the output of the warning signal. Thus, the suppress function may imply one or more of a delaying of the output of the warning signal, a prevention of the output of the warning signal or making the output of the warning signal dependent on one or more conditions to be fulfilled. Thus, the suppress function may be configured for stopping an arbitrary warning signal and/or for triggering an output of the warning signal or a further warning signal after a defined time interval, wherein the output, as an example, may only take place in case the further warning signal is still warranted after the defined time interval. Thus, the conditions to be fulfilled for the output of the warning signal as described above may have to be complied with. Otherwise, no warning signal may be output. The suppress function may also be referred to as "snooze function". For example, the sensor device may comprise at least one snooze button which may be configured to trigger the suppress function. The snooze function may have the advantage that the user may be reminded that he or she needs to react to the warning signal in case the user has no time to act at the moment the warning signal is output for the first time.

In a further aspect of the present disclosure, a sensor assembly for detecting at least one analyte in a body fluid of a user is disclosed. The term "sensor assembly" generally refers to a group of at least two elements or components which are capable of interacting in order to perform at least one sensor function, in the present case in order to perform at least one detection of the at least one analyte in the body fluid and/or in order to contribute to the at least one detection of the at least one analyte in the body fluid. The sensor assembly specifically may comprise an assembly of two or more components capable of interacting with each other, such as in order to perform one or more diagnostic purposes, such as in order to perform a medical analysis. The sensor assembly generally may also be referred to as a "sensor system" or as a "sensor kit."

The sensor assembly comprises the sensor device as described above or as will further be described below. Further, the sensor assembly comprises at least one sensor configured for monitoring a time-dependent concentration of the analyte in the body fluid. The sensor is operatively connected to the sensor device and is configured for providing a data stream of time-dependent measurement signals to the sensor device.

The term "sensor" may generally refer to an arbitrary element which is adapted to perform a process of detection and/or which is adapted to be used in the process of detection. Thus, the sensor specifically may be adapted to determine the concentration of the analyte and/or a presence of the analyte. The term "detection" generally refers to a process of determining a presence and/or a quantity and/or a concentration of the at least one analyte. Thus, the detection may be or may comprise a qualitative detection, simply determining the presence of the at least one analyte or the absence of the at least one analyte, and/or may be or may comprise a quantitative detection, which determines the quantity and/or the concentration of the at least one analyte. As a result of the detection, at least one signal may be produced which characterizes an outcome of the detection, such as at least one measurement signal. The at least one signal specifically may be or may comprise at least one electronic signal such as at least one voltage and/or at least one current. The at least one signal may be or may comprise at least one analog signal and/or may be or may comprise at least one digital signal. The sensor may also be referred to as "analyte sensor." Specifically, the sensor may be a glucose sensor being configured to determine a presence and/or quantity and/or a concentration of glucose in the body fluid of the user or the patient.

The term "operatively connected" may specifically refer to a state, wherein two or more objects are connected to each other such that they can interact with each other. Specifically, the sensor may be operably connected to the sensor device unit such that sensor signals of the sensor may be transmitted to the sensor device.

The sensor may be selected from the group consisting of a transcutaneous sensor and a subcutaneous sensor. The term "transcutaneous" generally refers to a property of an arbitrary element of being adapted to be fully or at least partly arranged through the body tissue of the patient or the user. For this purpose, the element may comprise an insertable portion. In order to further render the element to be usable as a transcutaneous element, the element may fully or partially provide a biocompatible surface, i.e., a surface which, at least during durations of use, does not have any detrimental effects on the user, the patient or the body tissue. Further, the transcutaneous element generally may be dimensioned such that a transcutaneous insertion of the element into the body tissue is feasible, such as by providing a width in a direction perpendicular to an insertion direction of no more than 5 mm, preferably of no more than 2 mm, more preferably of no more than 1.5 mm. Thus, the term "subcutaneous" may generally refer to a property of an arbitrary element of being situated or lying under the skin and within the body tissue of the user or the patient. Specifically, the object may be configured to be introduced under the skin, for example, as an injection. Further, the sensor may be a non-invasive sensor. The term "non-invasive" may refer to a property of an arbitrary element of being located outside the body of the patient, e.g., positioned or attached to a part of a body of the patient, wherein the part referred to a skin side or to a part which is accessible without a need of entering the part of the body with a penetrating element such as a needle, a catheter or other instruments. For example, the non-invasive sensor may be part of an inhalation sensor device and/or of a spectroscopic device for spectroscopically detecting one or more analytes in a body fluid from the outside of the patient's body, e.g., for oxygen measurement.

Specifically, the sensor may be an electrochemical sensor. As used herein, an "electrochemical sensor" generally is a sensor which is configured to conduct an electrochemical measurement in order to detect the at least one analyte contained in the body fluid. The term "electrochemical measurement" refers to a detection of an electrochemically detectable property of the analyte, such as an electrochemical detection reaction. Thus, for example, the electrochemical detection reaction may be detected by comparing one or more electrode potentials. The electrochemical sensor specifically may be adapted to and/or may be usable to generate at least one electrical sensor signal which directly or indirectly indicates the presence and/or the extent of the electrochemical detection reaction, such as at least one current and/or at least one voltage. The detection may be analyte-specific. The measurement may be a qualitative and/or a quantitative measurement. Still, other embodiments are feasible. The analyte sensor may comprise at least three electrodes such as at least one working electrode, comprising at least one test chemical being sensitive to the analyte to be detected, at least one reference electrode and at least one counter electrode. However, other embodiments are feasible.

The sensor assembly according to the present disclosure specifically may be used in a medical device. The medical device may comprise the sensor assembly as described above or as will further be described below. Further, the medical device may comprise at least one medication device configured for introducing at least one medication to a user. The term "medication device" may generally refer to an arbitrary device which is configured to interact with the user or the patient in order to provide a medication to the user. The term "medication" may specifically refer to an infusion, e.g., a liquid substance, specifically a liquid substance comprising a medicine. For example, the medication may be or may comprise insulin. Specifically, the medical device may be configured to introduce the medication transcutaneously and/or subcutaneously and/or in a non-invasive manner. Therefore, the medical device may comprise at least one infusion cannula. The term "infusion cannula" may generally refer to an arbitrary cannula being configured to introduce an infusion into a body tissue of an arbitrary patient, for example, directly into a vein of the patient. Therefore, the infusion cannula may be attached to a reservoir comprising the liquid substance, specifically via an ex vivo proximal end of the infusion cannula. Thus, besides of the infusion cannula, the medication device may further comprise at least one fluid coupling for coupling the medication device to at least one medication pump.

The medical device may be configured such that a detection of the analyte in the body fluid of the user and an intake of a medication via the medication device may be feasible. For example, the medication device and the sensor device may be configured to interact with each other. Specifically, the sensor device may be configured to transfer at least one signal to the medication device simultaneously to the point in time when the warning signal W is output.

The sensor device may be configured to communicate with the medication device via at least one communication device. The term "communication device" may refer to an arbitrary device which is configured to provide or enable a communication between two or more objects. Therefore, the communication device may be configured to transfer at least one signal, specifically at least one electronic signal from a first object to a second object or between the first object and the second object. The communication device may specifically be configured to enable a wireless communication, such as by radiofrequency, bluetooth or the like.

For example, the medical device and the sensor device may both be attached to the user on different skin sides of the user, specifically via at least one plaster. Thereby, the medication device may be configured to react to the medication signal by introducing a defined amount of medication to the patient automatically such as via the medication pump, i.e., without the need of an active action of the user or the patient.

Alternatively, the medical device may be an "external component." The term "external component" may refer to an arbitrary component which is part of a device but which forms a component of the device which is not physically connected to the device and may be handled independently. For example, the external component may be or may comprise at least one medication pen which is configured to supply an arbitrary medication to the user or the patient transcutaneously or subcutaneously via at least one infusion cannula. Specifically, the medication pen may be an infusion pen which is configured to supply a defined amount of insulin to the user or the patient. The sensor device may be configured to communicate wirelessly with the medication pen, specifically in order to provide at least one item of information about the defined amount of the medication which needs to be supplied to the user or the patient such that the concentration of the analyte in the body fluid falls back to and stays within the target range as described above. The medication pen is configured such that the user or the patient simply supplies the medication via applying the medication device, which includes inserting the insertion cannula into a skin site and pressing a button that is configured to trigger an insertion of the medication. However, the user or the patient does not need to worry about a dosage of the medication. Instead, the dosage may be adjusted automatically such as through the communication between the sensor device and the medication pen as described above.

In a further aspect of the present disclosure, a method for processing a data stream of a time-dependent concentration of an analyte in a body fluid of a user is disclosed. The method comprises the method steps described below. The method steps may be performed in the given order. However, other orders of the method steps are feasible. Further, one or more of the method steps may be performed in parallel and/or in a timely overlapping fashion. Further, one or more of the method steps may be performed repeatedly. Further, additional method steps may be present which are not listed.

The method comprises the following steps:
a) comparing a current value c(t) of the concentration with at least one first threshold value L and with at least one second threshold value H, with H>L;
b) defining a tolerance time interval;
c) detecting if the concentration rises and exceeds the first threshold value L during the tolerance time interval and preparing a warning signal W accordingly; and
d) suppressing an output of the warning signal W at least until the tolerance time interval expires, under the precondition that c(t)<H during the tolerance time interval.

Specifically, the method may comprise using the sensor device as described above or as will further be described below.

The disclosure further describes and proposes a computer program including computer-executable instructions for performing the method according to the present disclosure of one or more of the embodiments described herein when the program is executed on a computer or computer network. Specifically, the computer program may be stored on a computer-readable data carrier. Thus, specifically, one, more than one or even all of method steps a) to d) as indicated above may be performed by using a computer or a computer network, preferably by using a computer program.

The disclosure further describes and proposes a computer program product having program code means, in order to perform the method according to the present disclosure in one or more of the embodiments described herein when the program is executed on a computer or computer network. Specifically, the program code means may be stored on a computer-readable data carrier.

Further, the present application discloses and proposes a data carrier having a data structure stored thereon, which, after loading into a computer or computer network, such as into a working memory or main memory of the computer or computer network, may execute the method according to one or more of the embodiments disclosed herein.

The disclosure further proposes and describes a computer program product with program code means stored on a machine-readable carrier, in order to perform the method according to one or more of the embodiments disclosed herein, when the program is executed on a computer or computer network. As used herein, a computer program product refers to the program as a flexible product. The product may generally exist in an arbitrary format, such as in a paper format, or on a computer-readable data carrier. Specifically, the computer program product may be distributed over a data network.

Finally, this disclosure proposes and describes a modulated data signal which contains instructions readable by a computer system or computer network, for performing the method according to one or more of the embodiments disclosed herein.

Preferably, referring to the computer-implemented aspects of the disclosure, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, the present application further discloses:
A computer or computer network comprising at least one processor, wherein the processor is adapted to perform the method according to one of the embodiments described in this description,
a computer loadable data structure that is adapted to perform the method according to one of the embodiments described in this description while the data structure is being executed on a computer,
a computer program, wherein the computer program is adapted to perform the method according to one of the embodiments described in this description while the program is being executed on a computer,
a computer program comprising program means for performing the method according to one of the embodiments described in this description while the computer program is being executed on a computer or on a computer network,
a computer program comprising program means according to the preceding embodiment, wherein the program means are stored on a storage medium readable to a computer,
a storage medium, wherein a data structure is stored on the storage medium and wherein the data structure is adapted to perform the method according to one of the embodiments described in this description after having been loaded into a main and/or working storage of a computer or of a computer network, and
a computer program product having program code means, wherein the program code means can be stored or are stored on a storage medium, for performing the method according to one of the embodiments described in this description, if the program code means are executed on a computer or on a computer network.

The proposed sensor device, the proposed sensor assembly and the proposed method for processing a data stream of a time-dependent concentration show many advantages over known devices and methods.

Commonly, the patient or the user may simply suppress or ignore a warning signal when using common sensor devices. This may, for example, be the case, when the warning signal is output often and the user does not take the warning signal seriously.

By applying the sensor device according to the present disclosure, the user may get feedback on health status specifically in dependence of the tolerance time, the first threshold value, the second threshold value and optionally also in dependence of the offset value and/or further parameters. These parameters may, for example, be adaptable and/or adjustable to the needs and/or the health status of the user. Therefore, the user may receive a reliable warning signal which indicates for the user that measures have to be taken to decrease the concentration to the target range.

Summarizing the findings of the present disclosure, the following embodiments are preferred:

Embodiment 1: A sensor device for detecting at least one analyte in a body fluid of a user, the sensor device comprising at least one evaluation device configured for evaluating a data stream of time-dependent concentrations of the analyte, wherein the evaluation device comprises at least one comparator device configured for comparing a current value $c(t)$ of the concentration with at least one first threshold value L and with at least one second threshold value H, with H>L, wherein the evaluation device, by using the comparator device, is configured to detect if the concentration rises and exceeds the first threshold value L during the tolerance time interval, e.g., at at least one point in time $t_0$, and to prepare a warning signal W accordingly, wherein the evaluation device is further configured to define a tolerance time interval, wherein the evaluation device is configured to suppress an output of the warning signal W at least until the tolerance time interval expires, under the precondition that $c(t)<H$ during the tolerance time interval.

Embodiment 2: The sensor device according to the preceding embodiment, wherein the evaluation device further comprises at least one data storage device configured for storing a tolerance time value $\Delta t$.

Embodiment 3: The sensor device according to the preceding embodiment, wherein the evaluation device is configured to preliminarily define the tolerance time interval as $[t_0; t_0+\Delta t]$.

Embodiment 4: The sensor device according to any one of the two preceding embodiments, wherein the evaluation device is configured to define the tolerance time value $\Delta t$ according to one of the following options:
a default value is used and stored in the data storage device;
the tolerance time value $\Delta t$ is personally adjusted for the user and is stored in the data storage device; or
the tolerance time value $\Delta t$ is manually adjusted by the user.

Embodiment 5: The sensor device according to any one of the preceding embodiments, wherein the evaluation device further is configured to recognize at least one point of time $t_1$ at which an event known to have an effect lowering the concentration of the analyte occurs.

Embodiment 6: The sensor device according to the preceding embodiment, wherein the event known to have an effect lowering the concentration of the analyte is selected from the group consisting of: an intake of a medication, specifically an insulin medication; or a physical activity of the user, specifically sports.

Embodiment 7: The sensor device according to any one of the two preceding embodiments, wherein the evaluation device is configured to define an offset time interval starting at $t_1$, wherein the evaluation device is configured to suppress the output of the warning signal W at least until, additionally, the offset time interval is expired, under the precondition that $c(t)<H$ during the offset time interval.

Embodiment 8: The sensor device according the preceding embodiment, wherein the evaluation device is configured to perform one of the following operations during the offset time interval
(a) the warning signal W is always provided when $c(t)$ exceeds the second threshold value H; or
(b) the warning signal W is never provided when $c(t)$ exceeds the second threshold value H.

Embodiment 9: The sensor device according to any one of the two preceding embodiments, wherein the evaluation device is configured to perform one of the following operations:
(a) the tolerance time interval is unaffected by the offset time interval, and the output of the warning signal W is suppressed at least until both of the tolerance time interval and the offset time interval have expired;
(b) the tolerance time interval is suspended until expiry of the offset time interval and restarted for a remaining time after the offset time has expired; or
(c) the tolerance time interval is reinitialized at $t_1$, preferably by defining an updated tolerance time interval as $[t_1; t_1+\Delta t]$ with $\Delta t$ being the tolerance time value.

Embodiment 10: The sensor device according to any one of the two preceding embodiments, wherein the evaluation device is configured to choose a length of the offset time interval according to one of the following options:
a default value is used for the length of the offset time interval;
a length of the offset time interval adjusted by the user is chosen;
a length of the offset time interval is selected personally for the user;
a length of the offset time interval is calculated automatically by taking into account a nature of the event known to have an effect lowering the concentration of the analyte, specifically by taking into account a bolus of a medication, more specifically by taking into account an insulin bolus.

Embodiment 11: The sensor device according to any one of the preceding embodiments, wherein the evaluation device is configured to output the warning signal W if the concentration c exceeds the first threshold value L after the tolerance time interval expires and if the current value $c(t)$ of the concentration c is below the second threshold value H during the tolerance time interval. The evaluation device is further configured to output the warning signal W if concentration c exceeds H at any time.

Embodiment 12: The sensor device according to any one of the preceding embodiments, wherein the evaluation device, by using the comparator device, is configured for detecting if the concentration falls below the first threshold value L during the tolerance time interval.

Embodiment 13: The sensor device according to the preceding embodiment, wherein the evaluation device is configured to perform one of the following operations:
the expiry of the tolerance time interval is aborted when the concentration falls below the first threshold value L and the output of the warning signal W is prevented;
the expiry of the tolerance time interval is suspended as long as the concentration is below the first threshold value L;
the expiry of the tolerance time interval is slowed down during times in which the concentration is below the first threshold value L; or
the expiry of the tolerance time interval is reset after the time in which the concentration is below the first threshold value L reaches a predetermined threshold.

Embodiment 14: The sensor device according to any one of the preceding embodiments, wherein the evaluation device, by using the comparator device, is configured to detect if the concentration exceeds the second threshold value H during the tolerance time interval and to prepare a high level warning signal WH accordingly.

Embodiment 15: The sensor device according to the preceding embodiment, wherein the evaluation device further is configured to recognize at least one point of time $t_1$ at which an event known to have an effect lowering the concentration of the analyte occurs, specifically an event selected from the group consisting of an intake of a medication, specifically an insulin medication or a physical activity of the user, specifically sports, wherein the evaluation device is configured to define a high level offset time interval starting at $t_1$, wherein the evaluation device is configured to suppress an output of the high level warning signal WH at least until the high level offset time interval is expired.

Embodiment 16: The sensor device according to any one of the preceding embodiments, wherein the sensor device is configured for receiving a data stream of time-dependent measurement signals from at least one sensor configured for monitoring the time-dependent concentration of the analyte in a body fluid.

Embodiment 17: The sensor device according to the preceding embodiment, wherein the evaluation device is configured to transform the data stream of the time-dependent measurement signals into the data stream of time-dependent concentrations of the analyte.

Embodiment 18: The sensor device according to any one of the preceding embodiments, wherein the sensor device further comprises at least one database, wherein data stream of time-dependent concentrations of the analyte are stored in the database.

Embodiment 19: The sensor device according to the preceding embodiment, wherein the database further comprises additional information on events having an influence on the concentration of the analyte.

Embodiment 20: The sensor device according to the preceding embodiment, wherein the additional information on the events having an influence on the concentration of the analyte comprises at least one item of information selected from the group consisting of: a bolus of insulin; a physical activity of the user, specifically sports; or an intake of nutrition.

Embodiment 21: The sensor device according to any one of the preceding embodiments, wherein the analyte is glucose.

Embodiment 22: A sensor assembly for detecting at least one analyte in a body fluid of a user, the sensor assembly comprising the sensor device according to any one of the preceding embodiments, the sensor assembly further comprising at least one sensor configured for monitoring a time-dependent concentration of the analyte in the body fluid, wherein the sensor is operatively connected to the sensor device and is configured for providing a data stream of time-dependent measurement signals to the sensor device.

Embodiment 23: The sensor assembly according to the preceding embodiment, wherein the sensor is selected from the group consisting of a transcutaneous sensor and a subcutaneous sensor.

Embodiment 24: The sensor assembly according to any one of the two preceding embodiments, wherein the sensor is an electrochemical sensor.

Embodiment 25: The sensor assembly according to any one of the three preceding embodiments, wherein the sensor is a glucose sensor.

Embodiment 26: A method for processing a data stream of a time-dependent concentration of an analyte in a body fluid of a user, the method comprising:
a) comparing a current value $c(t)$ of the concentration with at least one first threshold value L and with at least one second threshold value H, with H>L;
b) defining a tolerance time interval;
c) detecting if the concentration rises and exceeds the first threshold value L during the tolerance time interval, e.g., at at least one point in time $t_0$, and preparing a warning signal W accordingly; and
d) suppressing an output of the warning signal W at least until the tolerance time interval expires, under the precondition that $c(t)<H$ during the tolerance time interval.

Embodiment 27: The method according to the preceding embodiment, wherein the method comprises using the sensor device according to any one of the preceding embodiments referring to a sensor device.

Embodiment 28: A computer or computer network comprising at least one processor, wherein the processor is adapted to perform the method according to any one of the preceding embodiments referring to a method.

Embodiment 29: A computer loadable data structure that is adapted to perform the method according to any one of the preceding embodiments referring to a method while the data structure is being executed on a computer.

Embodiment 30: A computer program, wherein the computer program is adapted to perform the method according to any one of the preceding embodiments referring to a method while the program is being executed on a computer.

Embodiment 31: A computer program comprising program means for performing the method according to any one of the preceding embodiments referring to a method while the computer program is being executed on a computer or on a computer network.

Embodiment 32: A computer program comprising program means according to the preceding embodiment, wherein the program means are stored on a storage medium readable to a computer.

Embodiment 33: A storage medium, wherein a data structure is stored on the storage medium and wherein the data structure is adapted to perform the method according to any one of the preceding embodiments referring to a method after having been loaded into a main and/or working storage of a computer or of a computer network.

Embodiment 34: A computer program product having program code means, wherein the program code means can be stored or are stored on a storage medium, for performing the method according to any one of the preceding embodiments referring to a method when the program code means are executed on a computer or on a computer network.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following description. Rather, the embodiments are chosen and described so that others skilled in the art may appreciate and understand the principles and practices of this disclosure.

Figure 1:
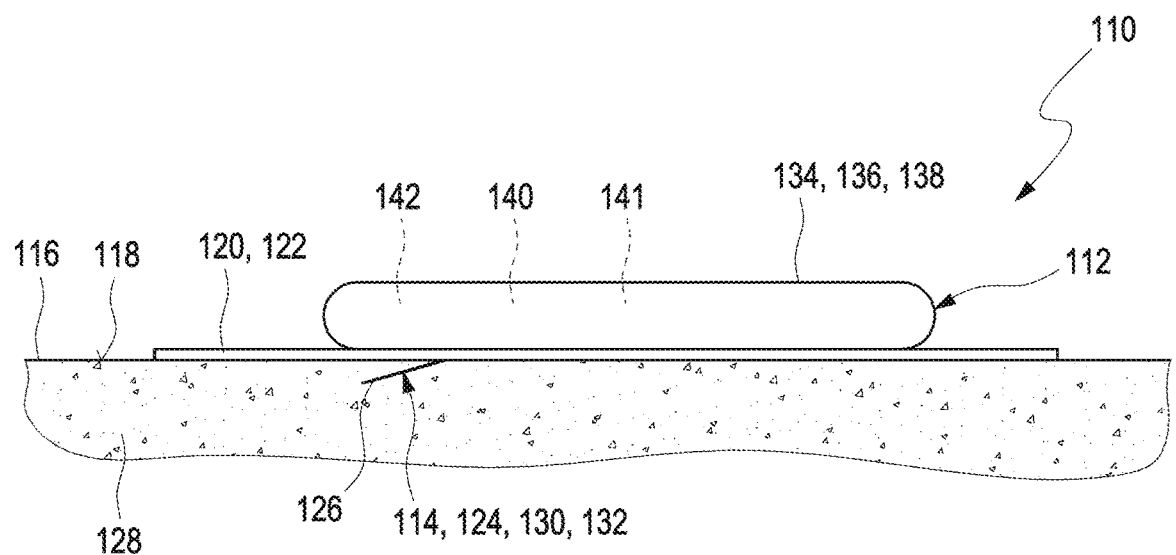
FIG. 1 shows an exemplary embodiment of a sensor assembly in a schematic illustration.

FIG. 1 shows an exemplary embodiment of a sensor assembly 110 in a schematic illustration. The sensor assembly 110 comprises at least one sensor device 112 for detecting at least one analyte in a body fluid of a user. Further, the sensor assembly 110 comprises at least one sensor 114 configured for monitoring a time-dependent concentration of the analyte in the body fluid.

The sensor assembly may 110 be fixedly applied to a skin side 116 of the user, specifically on a surface 118 of the skin side 116. For example, the sensor assembly 110 may be fixedly connected to the surface 118 of skin side 116 via at least one adhesive element 120 such as a plaster 122.

The sensor 114 is operatively connected to the sensor device 112 and is configured for providing a data stream of time-dependent measurement signals to the sensor device 112. Specifically, the sensor 114 may be a transcutaneous sensor 124. Therefore, the sensor 114 may comprise an insertable portion 126. The insertable portion 126 may be adapted to be fully or at least partly arranged through the skin side 116 of the patient or the user. Thus, the insertable portion 126 may be arranged within a body tissue 128 of the patient or the user.

The sensor 114 may specifically be an analyte sensor 130, more specifically a glucose sensor 132 being configured to determine a presence and/or quantity and/or a concentration of glucose in the body fluid of the user or the patient.

The sensor device 112 comprises at least one evaluation device 134 configured for evaluating a data stream of time-dependent concentrations of the analyte. The evaluation device 134 may also be referred to as control part 136 or as electronics unit 138. The evaluation device comprises at least one comparator device 140 configured for comparing a current value $c(t)$ of the concentration with at least one first threshold value L and with at least one second threshold value H, with H>L as will further be illustrated in FIGS. 2A to 2C and will further be described below.

Moreover, the evaluation device 134 may comprise at least one data storage device 141 configured for storing a tolerance time value $\Delta t$. Further, the sensor device 112 may comprise at least one database 142. Data stream of time-dependent concentrations of the analyte may be stored in the database 142. Specifically, the database 142 may further comprise additional information on events having an influence on the concentration of the analyte.

FIGS. 2A to 2D show time-dependent concentrations of an analyte in a body fluid in time-dependently in different scenarios, respectively. The time-dependent concentrations as shown in FIGS. 2A to 2D may, for example, be monitored via the sensor assembly 110 as illustrated within FIG. 1 and as described above.

Figure 2:
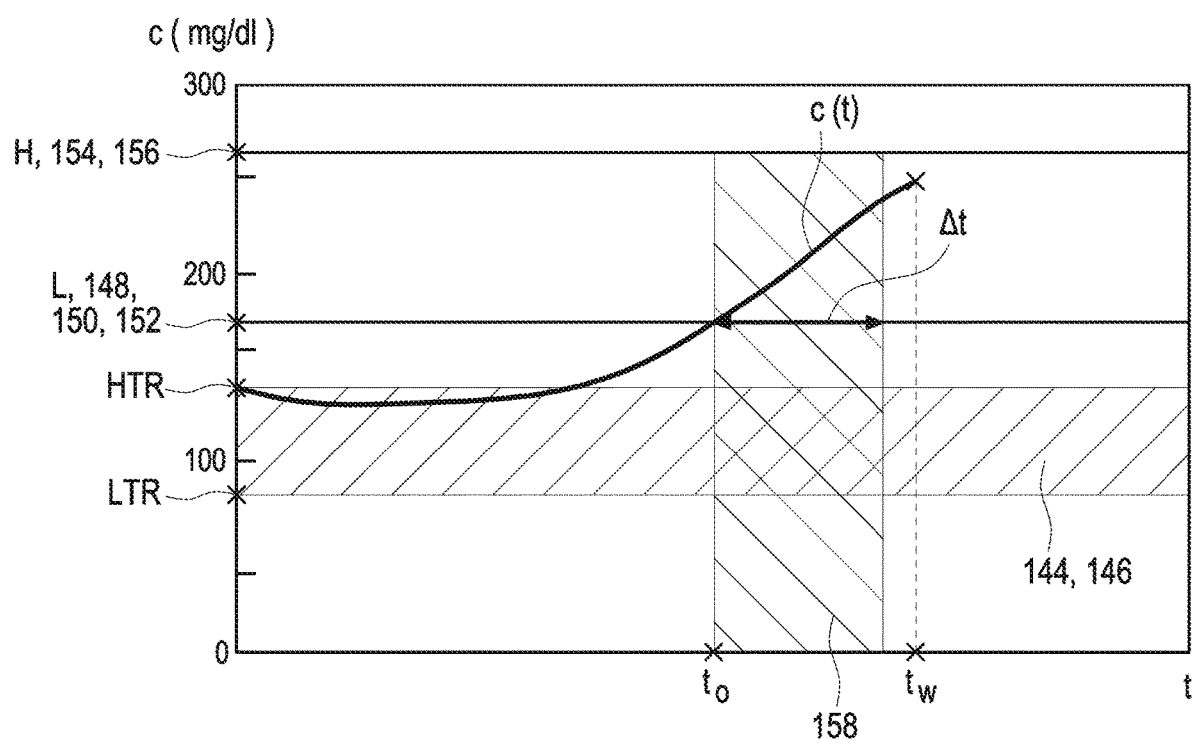
FIGS. 2A to 2D show concentrations of an analyte in a body fluid time-dependently in different scenarios, respectively.
Figure 2:
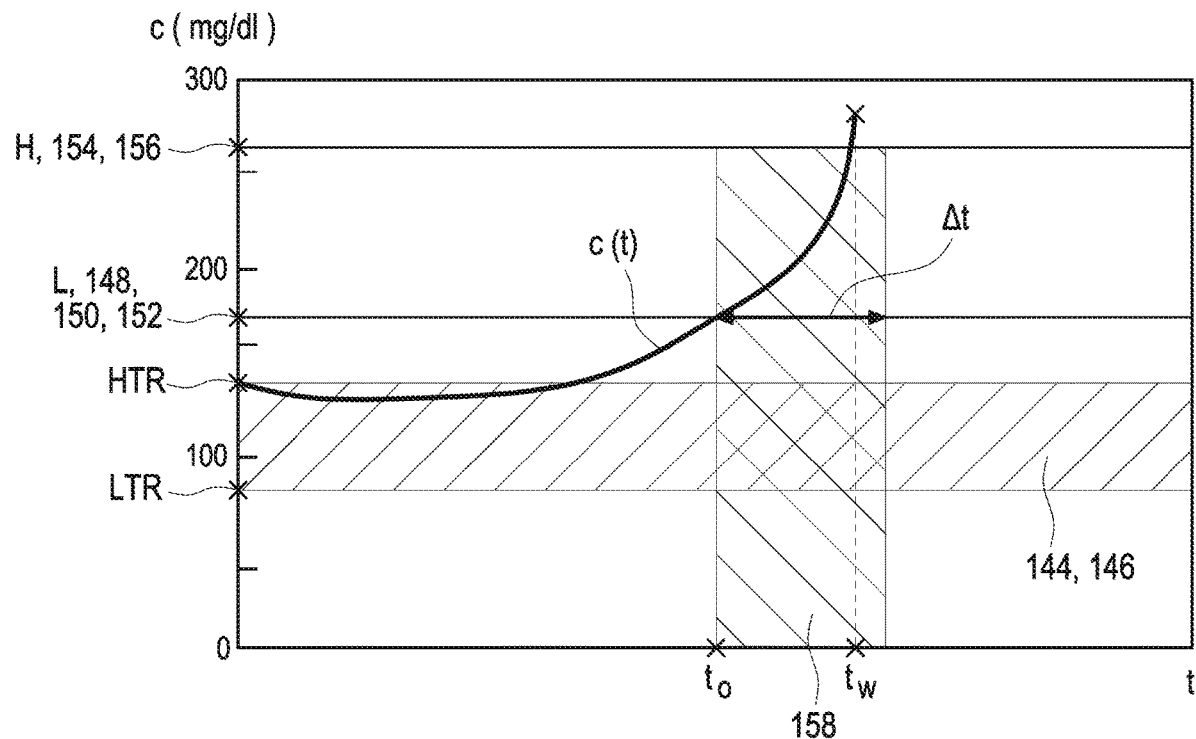
Figure 2:
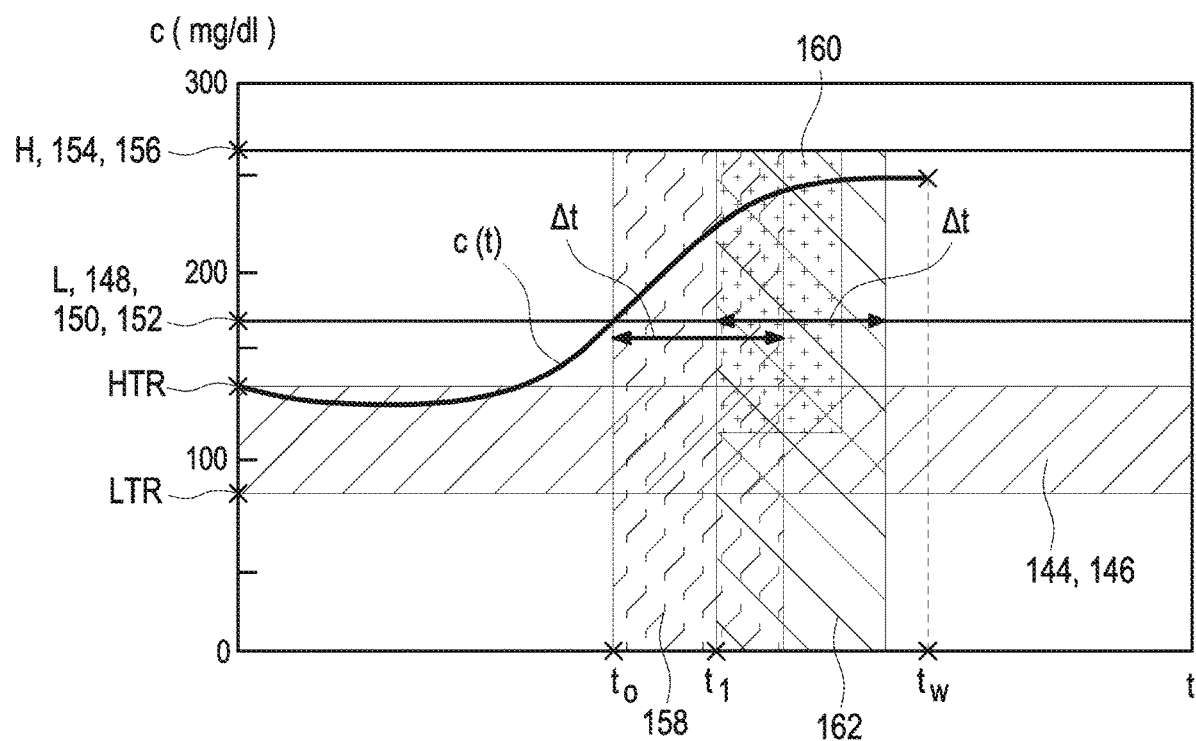
Figure 2:
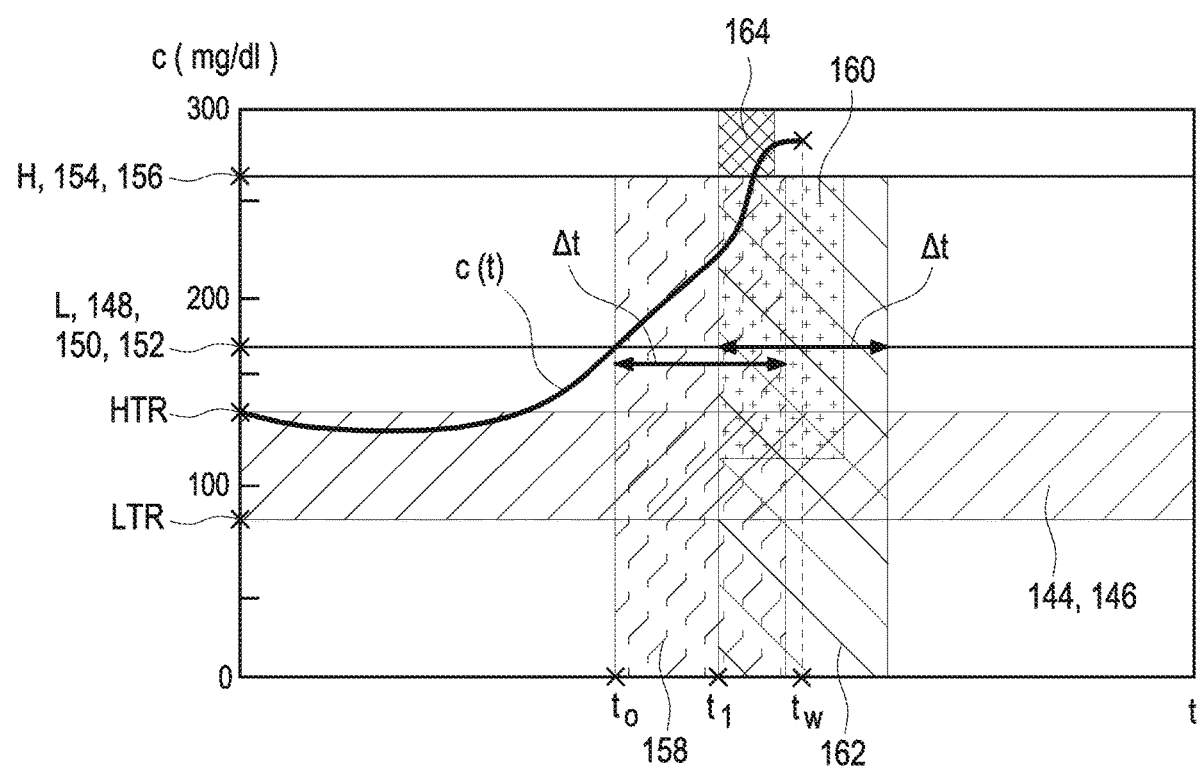

FIG. 2A shows a current values c(t) of the concentration c in dependence of the time t. For example, the current value c(t) may correspond to a glucose concentration within the body fluid, specifically within the blood, of the user or the patient. The unit of c(t) may be mg/dL.

Firstly, the current values c(t) may be within a target range 144. The target range 144 may be defined by a lower target range threshold value LTR and a higher target range threshold value HTR. The target range 144 may define a desired range 146 for the concentration c of the analyte in the body fluid. Thereby, the user or the patient may be in optimal healthy condition with regard to the concentration of the analyte in the body fluid.

The comparator device 140 as illustrated in FIG. 1 and as described above is configured for comparing the current value c(t) of the concentration c with at least one first threshold value L and with at least one second threshold value H. The first threshold value L may also be referred to as lower threshold value 148, as warning threshold value 150 or as high warning threshold value 152. Thereby, in case the concentration c exceeds the first threshold value L, this scenario may correspond to a health status of the user which is acceptable at least over a certain time interval but not optimal. Further, the second threshold value H may also be referred to as an alert threshold value 154 or as a high alert threshold value 156. Thereby, in case the concentration c exceeds the second threshold value H may correspond to a health state of the user which is not acceptable and during which the user or the patient may be in danger with regard to the health status. For example, the lower threshold value L may be slightly higher than the higher target range threshold value HTR of the target range 144.

In the exemplary scenario as depicted in FIG. 2A, the concentration c may rise and exceed the first threshold value L at a point in time $t_0$. The evaluation device 134 as depicted in FIG. 1 and as described above may be configured to prepare a warning signal accordingly. Further, the evaluation device 134 may be configured to define a tolerance time interval 158 with a tolerance time value $\Delta t$. The tolerance time value $\Delta t$ may, for example, be defined via a default value which is stored in the data storage device 141. Further, the tolerance time value $\Delta t$ may be personally adjusted for the user and may stored in the data storage device 141 or the tolerance time value $\Delta t$ may be manually adjusted by the user.

Thus, the evaluation device 134 may be configured to preliminary define the tolerance time interval as $[t_0; t_0+\Delta t]$. The evaluation device 134 may be configured to suppress an output of the warning signal at least until the tolerance time interval 158 expires, under the precondition that c(t)<H during the tolerance time interval 158. The warning signal may be output at a point in time denoted with $t_w$.

FIG. 2B shows current values c(t) of the concentration c in dependence of the time t. FIG. 2B corresponds at least in large parts to FIG. 2A. Thus, reference can be made to the description of FIG. 2A above. However, in the scenario as depicted in FIG. 2B, c(t) may exceed the second threshold value H within the tolerance time interval 158. Thereby, the warning signal may be output.

FIG. 2C shows current values c(t) of the concentration c in dependence of the time t. FIG. 2C corresponds at least in large parts to FIGS. 2A and 2B. Thus, reference can be made to the description of FIGS. 2A and 2B above.

In the scenario as depicted in FIG. 2C, in at least one point of time $t_1$ an event known to have an effect lowering the concentration of the analyte occurs. For example, the event may be an intake of a medication or a physical activity of the user. An offset time interval 160 starts at $t_1$. Thereby, the evaluation device 134 as illustrated in FIG. 1 may be configured to suppress the output of the warning signal W until, additionally, the offset time interval 160 is expired, under the precondition that c(t)<H during the offset time interval. In the scenario as depicted in FIG. 2C, the tolerance time interval 158 is reinitialized at $t_1$, specifically by defining an updated tolerance time interval 162 as $[t_1; t_1+\Delta t]$.

A length of the offset time interval 160 may, for example, be determined via a default value. Further, the length of the offset time interval 160 may be adjusted by the user or may be selected personally for the user. Alternatively, the length of the offset time interval may be calculated automatically by taking into account a nature of the event known to have an effect lowering the concentration of the analyte.

FIG. 2D shows current values c(t) of the concentration c in dependence of the time t. FIG. 2D corresponds at least in large parts to FIG. 2C. Thus, reference can be made to the description of FIG. 2C above.

In the scenario as depicted in FIG. 2D, a high level offset time interval 164 is defined starting at $t_1$. The evaluation device 134 may be configured to recognize at $t_1$, an event known to have an effect lowering the concentration c of the analyte occurs, such as an intake of a medication. During the high level offset time interval 164 the output of a high level warning signal may be suppressed. Typically, a length of the high level offset time interval 164 may be smaller than the length of the offset time interval 160.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this disclosure pertains and which fall within the limits of the appended claims.

LIST OF REFERENCE NUMBERS 110 sensor assembly
112 sensor device
114 sensor
116 skin side
118 surface
120 adhesive element
122 plaster
124 transcutaneous sensor
126 insertable portion
128 body tissue
130 analyte sensor
132 glucose sensor
134 evaluation device
136 control part
138 electronics unit
140 comparator device
141 data storage device 142 database
144 target range
146 desired range
148 lower threshold value
150 warning threshold value
152 high warning threshold value
154 alert threshold value
156 high alert threshold value
158 tolerance time interval
160 offset time interval
162 updated tolerance time interval
164 high level offset time interval

What is claimed is:

1. A sensor device for detecting at least one analyte in a body fluid of a user, the sensor device comprising:
at least one evaluation device configured for evaluating a data stream of time-dependent concentrations c of the analyte, wherein the evaluation device comprises at least one comparator device configured for comparing a current value c(t) of the concentration c with a first threshold value L and with a second threshold value H, wherein H>L, wherein the evaluation device is further configured to define a tolerance time interval, the tolerance time interval beginning when the concentration c intersects the first threshold value L and wherein the evaluation device is configured to prepare a warning signal W if the comparator device detects that the concentration c rises and exceeds the first threshold value L during the tolerance time interval, and wherein the evaluation device is configured to suppress output of the warning signal W at least until the tolerance time interval expires, provided that c(t)<H during the tolerance time interval;
wherein the evaluation device is configured to define a separate offset time interval starting at t1, and the evaluation device is configured to suppress the output of the warning signal W at least until the offset time interval is expired, provided that c(t)<H during the offset time interval; and
further comprising a medication device wherein the sensor device is configured to communicate with the medication device and the medication device is configured to deliver insulin to the user and a dosage of the insulin delivered to the user by the medication device is determined as a function of information communicated from the sensor device to the medication device.

2. The sensor device according to claim 1, wherein the evaluation device further comprises at least one data storage device configured for storing a tolerance time value $\Delta t$.

3. The sensor device according to claim 2, wherein the evaluation device is configured to define the tolerance time value $\Delta t$ according to one of the following:
a default value is used and stored in the data storage device;
the tolerance time value $\Delta t$ is personally adjusted for the user and is stored in the data storage device; or
the tolerance time value $\Delta t$ is manually adjusted by the user.

4. The sensor device according to claim 1, wherein the evaluation device further is configured to recognize at least one point of time t1 at which an event known to have an effect lowering the concentration c of the analyte occurs.

5. The sensor device according to claim 4, wherein the event known to have an effect lowering the concentration c of the analyte is selected from the group consisting of: an intake of a medication; or a physical activity of the user.

6. The sensor device according to claim 1, wherein the evaluation device is configured to always provide the warning signal W when c(t) exceeds the second threshold value H during the offset time interval.

7. The sensor device according to claim 1, wherein the evaluation device is configured to never provide the warning signal W when c(t) exceeds the second threshold value H during the offset time interval.

8. The sensor device according to claim 1, wherein the evaluation device is configured to perform one of the following operations:
the tolerance time interval is unaffected by the offset time interval, and the output of the warning signal W is suppressed at least until both of the tolerance time interval and the offset time interval have expired;
the tolerance time interval is suspended until expiry of the offset time interval and restarted for a remaining time after the offset time has expired; or
the tolerance time interval is reinitialized at t1.

9. The sensor device according to claim 1, wherein the tolerance time interval is reinitialized at t1 by defining an updated tolerance time interval as t1+$\Delta t$ wherein $\Delta t$ is the tolerance time value.

10. The sensor device according to claim 1, wherein the evaluation device is configured to choose a length of the offset time interval according to one of the following options:
a default value is used for the length of the offset time interval;
a length of the offset time interval adjusted by the user is chosen;
a length of the offset time interval is selected personally for the user; or
a length of the offset time interval is calculated automatically by taking into account a nature of the event known to have an effect lowering the concentration of the analyte.

11. The sensor device according to claim 10 wherein a length of the offset time interval is calculated automatically by taking into account a nature of the event known to have an effect lowering the concentration of the analyte.

12. The sensor device according to claim 1, wherein the evaluation device is configured to output the warning signal W if the concentration c exceeds the first threshold value L after the tolerance time interval expires and if the current value c(t) of the concentration c remained below the second threshold value H during the tolerance time interval and wherein the evaluation device is further configured to output the warning signal W, if the concentration c exceeds H at any time.

13. The sensor device according to claim 1, wherein, if the comparator device detects that the concentration c falls below the first threshold value L during the tolerance time interval, the evaluation device is configured to perform one of the following operations:
the expiry of the tolerance time interval is aborted when the concentration c falls below the first threshold value L and the output of the warning signal W is prevented;
the expiry of the tolerance time interval is suspended as long as the concentration c is below the first threshold value L;
the expiry of the tolerance time interval is slowed down during times in which the concentration c is below the first threshold value L; or
the expiry of the tolerance time interval is reset after the time in which the concentration c is below the first threshold value L reaches a predetermined threshold.

14. A sensor device for detecting at least one analyte in a body fluid of a user, the sensor device comprising:
at least one evaluation device configured for evaluating a data stream of time-dependent concentrations c of the analyte, wherein the evaluation device comprises at least one comparator device configured for comparing a current value c(t) of the concentration c with a first threshold value L and with a second threshold value H, wherein H>L, wherein the evaluation device is further configured to define a tolerance time interval, the tolerance time interval beginning when the concentration c intersects the first threshold value L and wherein the evaluation device is configured to prepare a warning signal W if the comparator device detects that the concentration c rises and exceeds the first threshold value L during the tolerance time interval, and wherein the evaluation device is configured to suppress output of the warning signal W at least until the tolerance time interval expires, provided that c(t)<H during the tolerance time interval;
wherein the evaluation device is configured to delay the expiry of the tolerance time interval as a function of the time period in which the concentration c is below the first threshold value L during the tolerance time interval; and
further comprising a medication device wherein the sensor device is configured to communicate with the medication device and the medication device is configured to deliver insulin to the user and a dosage of the insulin delivered to the user by the medication device is determined as a function of information communicated from the sensor device to the medication device.

15. The sensor device according to claim 1 wherein the evaluation device suspends expiry of the tolerance time interval when the concentration c is below the first threshold value L during the tolerance time interval.

16. The sensor device according to claim 1, wherein the evaluation device prepares a high level warning WH if the comparator device detects that the concentration c exceeds the second threshold value H during the tolerance time and wherein the evaluation device further is configured to recognize at least one point of time t1 at which an event known to have an effect lowering the concentration c of the analyte occurs, wherein the evaluation device defines a high level offset time interval starting at t1, wherein the evaluation device suppresses an output of the warning signal W and the high level warning signal WH at least until the high level offset time interval is expired.

17. The sensor device according to claim 1, wherein the sensor device is configured for receiving a data stream of time-dependent measurement signals from at least one sensor configured for monitoring the time-dependent concentration c of the analyte in a body fluid, wherein the evaluation device is configured to transform the data stream of the time-dependent measurement signals into the data stream of time-dependent concentrations c of the analyte.

18. A sensor assembly for detecting at least one analyte in a body fluid of a user, the sensor assembly comprising the sensor device according to claim 1, the sensor assembly further comprising at least one sensor configured for monitoring a time-dependent concentration c of the analyte in the body fluid, wherein the sensor is operatively connected to the sensor device and is configured for providing a data stream of time-dependent measurement signals to the sensor device.

19. The sensor device according to claim 1, wherein output of all warning signals W is prevented as a result of the concentration c intersecting the first threshold value L to start the tolerance time interval if c(t)<H during the tolerance time interval and c(t) is less than L at the expiry of the tolerance time interval.

20. The sensor device according to claim 1, wherein the tolerance time interval is suspended until expiry of the offset time interval and restarted for a remaining time after the offset time has expired.

21. The sensor device according to claim 1, wherein the sensor device is configured to generate a signal representing a dosage of insulin to be delivered to the user.

22. The sensor device according to claim 21, wherein the sensor device communicates the signal wirelessly.

23. The sensor device according to claim 22, wherein the medication device is configured to wirelessly receive the signal from the sensor device.

24. A method for processing a data stream of a time-dependent concentration c of an analyte in a body fluid of a user using a sensor device for detecting the analyte wherein the sensor device includes at least one evaluation device configured for evaluating a data stream of time-dependent concentrations c of the analyte and the evaluation device includes at least one comparator device; the method comprising:
comparing a current value c(t) of the concentration c with a first threshold value L and with a second threshold value H, wherein H>L using the comparator device;
defining a tolerance time interval using the evaluation device;
detecting if the concentration c rises and exceeds the first threshold value L during the tolerance time interval and preparing a warning signal W if the concentration exceeds the first threshold value L;
suppressing an output of the warning signal W during the tolerance time interval provided that c(t)<H during the tolerance time interval;
defining a separate offset time interval starting at t1 and suppressing the output of the warning signal W at least until the offset time interval is expired, provided that c(t)<H during the offset time interval;
determining a dosage of medication for the user based at least in part on the concentration of the analyte wherein the analyte is glucose and the medication is insulin; and
delivering the dosage of medication to the user.

* * * * *